(12) United States Patent
Sisk

(10) Patent No.: US 9,954,184 B2
(45) Date of Patent: Apr. 24, 2018

(54) ELECTRON TRANSPORT MATERIAL FOR ORGANIC EMITTING DIODES

(71) Applicant: Nitto Denko Corporation, Osaka (JP)

(72) Inventor: David T. Sisk, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 243 days.

(21) Appl. No.: 14/738,634

(22) Filed: Jun. 12, 2015

(65) Prior Publication Data

US 2015/0364699 A1   Dec. 17, 2015

Related U.S. Application Data

(60) Provisional application No. 62/012,098, filed on Jun. 13, 2014.

(51) Int. Cl.
*H01L 51/00* (2006.01)
*C07D 215/12* (2006.01)
*C07D 241/42* (2006.01)
*H01L 51/50* (2006.01)

(52) U.S. Cl.
CPC ........ *H01L 51/0072* (2013.01); *C07D 215/12* (2013.01); *C07D 241/42* (2013.01); *H01L 51/5072* (2013.01)

(58) Field of Classification Search
CPC ............ H10L 51/0072; H10L 51/5072; H10L 51/5048; H10L 51/5056; H10L 51/5064; H10L 51/5068; H10L 51/5076; H10L 51/508; H10L 51/5084; C07D 215/12; C07D 215/42; C07D 401/14
USPC ............ 428/690; 257/40; 546/138, 140, 173
See application file for complete search history.

(56) References Cited

U.S. PATENT DOCUMENTS

2013/0285021 A1* 10/2013 Jenekhe ............... C07D 215/06
257/40

* cited by examiner

*Primary Examiner* — Ruiyun Zhang
(74) *Attorney, Agent, or Firm* — K&L Gates LLP; Louis C. Cullman; Robert W. Winn

(57) ABSTRACT

Some embodiments provide a compound represented by Formula 1, wherein $ET_1$, $ET_2$ and $ET_3$ are optionally substituted quinolinyl or optionally substituted quinoxalinyl; and wherein $R_1$, $R_2$, and $R_3$ are independently selected from the group consisting of H, $C_{1-3}$ alkyl, and $C_{1-3}$ perfluoroalkyl. Other embodiments provide an organic electron transmission element and an organic light-emitting diode device comprising a compound of Formula 1.

9 Claims, 1 Drawing Sheet

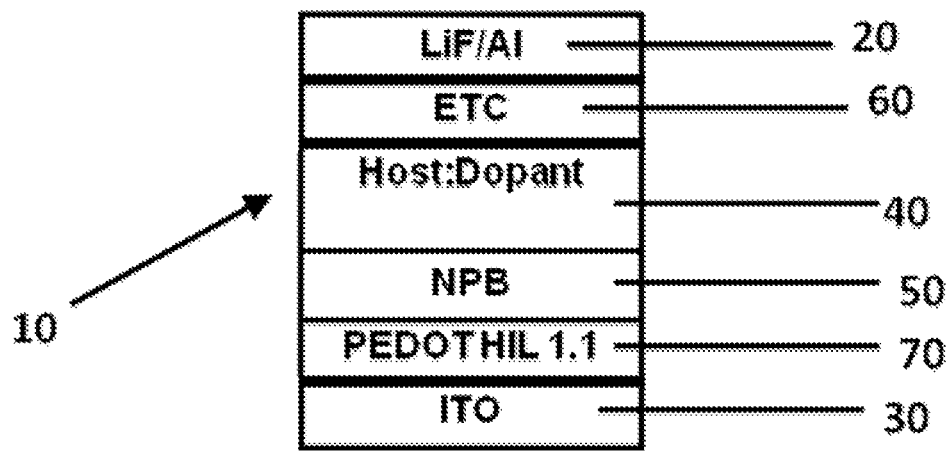

ELECTRON TRANSPORT MATERIAL FOR ORGANIC EMITTING DIODES

This application claims priority to U.S. 62/012,098 filed Jun. 13, 2014, the entire disclosure of which is incorporated by reference herein.

BACKGROUND

Field

The present disclosure generally relates to the fields of organic chemistry and organic light emitting diode materials. More specifically, the present disclosure represents a development of a new electron transport material to be used in Organic Light Emitting Diode (OLED) applications.

Description of the Related Art

Organic light-emitting devices have been widely developed for flat panel displays, and are moving fast toward solid state lighting (SSL) applications. Organic Light Emitting Diodes (OLEDs) comprise a cathode, a hole-transporting layer, an emissive layer, an electron-transporting layer, and an anode. Light emitted from an OLED device is the result of recombination of positive charges (holes) and negative charges (electrons) inside an organic (emissive) layer. The holes and electrons combine within a single molecule or a small cluster of molecules to generate excitons, which are molecules in an excited state, or groups of organic molecules bound together in an excited state. When the organic molecules release the required energy and return to their stable state, photons are generated. Current limitations on the commercialization of OLED technology for general lighting, display and niche applications include subpar device efficiency, lifetime, and color quality. As a result there is a need for improving OLED device architecture and the development of new organic materials for the interlayers of OLED devices.

SUMMARY

In accordance with the purposes of the present disclosure, as embodied and broadly described herein, the present disclosure includes a compound for use in OLEDs that functions as an electron-transport material.

Some embodiments include compound represented by Formula 1:

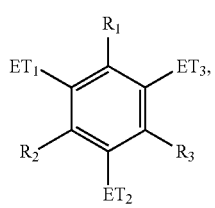

Formula 1 wherein $ET_1$, $ET_2$, and $ET_3$ are independently optionally substituted quinolinyl or optionally substituted quinoxalinyl, wherein the quinolinyl or quinoxalinyl attaches at a carbon atom of the benzo-ring; and $R_1$, $R_2$, and $R_3$ are independently H, $C_{1-3}$ alkyl, or $C_{1-3}$ perfluoroalkyl.

Some embodiments include a compound that is optionally substituted 1,3,5-tri(quinoxalinyl-5-yl)benzene, optionally substituted 1,3,5-tri(quinolin-8-yl)benzene, or optionally substituted 1,3,5-tri(quinolin-5-yl)benzene.

Some embodiments include an electron-transporting element comprising a compound described herein, such as a compound of Formula 1, optionally substituted 1,3,5-tri(quinoxalinyl-5-yl)benzene, optionally substituted 1,3,5-tri(quinolin-8-yl)benzene, or optionally substituted 1,3,5-tri(quinolin-5-yl)benzene.

Some embodiments include an organic light-emitting diode device comprising: (1) a cathode; (2) an anode; (3) a light-emitting layer disposed between and electrically connected to the anode and the cathode; and an electron-transport layer comprising a compound described herein, such as a compound of Formula 1, optionally substituted 1,3,5-tri(quinoxalinyl-5-yl)benzene, optionally substituted 1,3,5-tri(quinolin-8-yl)benzene, or optionally substituted 1,3,5-tri(quinolin-5-yl)benzene, disposed between and electrically connected to the cathode and the light-emitting layer.

These and other embodiments are described in greater detail below.

BRIEF DESCRIPTION OF THE DRAWINGS

FIG. 1 is a schematic of a device incorporating an embodiment of a compound described herein.

DETAILED DESCRIPTION

By employing a newly designed molecular structure, an example of which is shown below, a series of emissive electron-transport materials are described that can be used in OLED device applications.

As used herein, the term "quinolinyl" refers to the ring system:

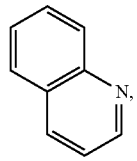

which includes, but is not limited to:

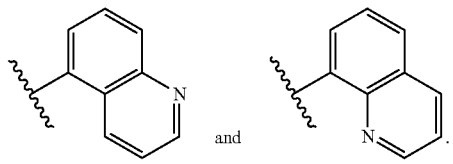 [SMILES: *c1cccc2ncccc12 ; *c1cccc2cccnc12]

and

As used herein, the term "optionally substituted quinolinyl" includes both an unsubstituted quinolinyl and a substituted quinolinyl. In a substituted quinolinyl, one or more hydrogen atoms on the ring system are independently replaced by one or more substituent groups indicated herein.

As used herein, the term "quinoxalinyl" refers to the ring system:

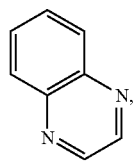

which includes, but is not limited to:

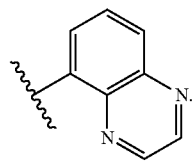 [SMILES: *c1cccc2nccnc12]

As used herein, the term "optionally substituted quinoxalinyl" includes both an unsubstituted quinoxalinyl and a substituted quinoxalinyl. In a substituted quinoxalinyl, one or more hydrogen atoms on the ring system are independently replaced by one or more substituent groups indicated herein.

As used herein, the term "aryl" as used herein refers to an aromatic ring or ring system. Exemplary non-limiting aryl groups are phenyl, naphthyl, etc.

As used herein, the term "perfluoroalkyl" refers to a fluoroalkyl with a formula $C_nF_{2n+1}$ for a linear or branched structure, e.g., $CF_3$, $C_2F_5$, $C_3F_7$, $C_4F_9$, $C_5F_{11}$, $C_6F_{13}$, etc., or $C_nF_{2n-1}$ for a cyclic structure, e.g., cyclic $C_3F_5$, cyclic $C_4F_7$, cyclic $C_5F_9$, cyclic $C_6F_{11}$, etc. In other words, every hydrogen atom in alkyl is replaced by fluorine. For example, while not intending to be limiting, $C_{1-3}$ perfluoroalkyl refers to $CF_3$, $C_2F_5$, and $C_3F_7$ isomers.

As used herein, the term "alkyl" refers to a hydrocarbon moiety lacking double or triple bonds. Examples include, but are not limited to, linear alkyl, branched alkyl, cycloalkyl, or combinations thereof. Alkyl may also be defined by the following general formulas: the general formula for linear or branched alkyl is $C_nH_{2n+1}$, and the general formula for an alkyl containing one ring is $C_nH_{2n-1}$. A $C_{X-Y}$ alkyl or $C_X$-$C_Y$ alkyl is an alkyl having from X to Y carbon atoms. For example, $C_{1-3}$ alkyl or $C_1$-$C_3$ alkyl includes fully saturated hydrocarbon containing 1, 2, or 3 carbon atoms.

As used herein, the term "optionally substituted" is used to denote a group that may be substituted or unsubstituted. A substituted group is derived from the unsubstituted parent structure wherein one or more hydrogen atoms on the parent structure have been independently replaced by one or more substituents. A substituted group may have one or more substituents on the parent group structure. Some substituents may independently be represented by a formula $C_{0-12}H_{0-25}O_{0-3}N_{0-2}F_{0-5}Cl_{0-1}$ $Br_{0-1}$, $C_{0-6}H_{0-20}O_{0-3}N_{0-2}F_{0-5}Cl_{0-1}Br_{0-1}$, $C_{0-4}H_{0-12}O_{0-2}N_{0-1}F_{0-3}Cl_{0-1}$, $C_{0-4}H_{0-12}O_{0-1}N_{0-1}F_{0-1}Cl_{0-1}$, or $C_{0-4}H_{0-12}O_{0-1}N_{0-1}F_{0-1}Cl_{0-1}$, provided that each substituent has at least one non-hydrogen atom, or may have a molecular weight of about 15 Da to about 50 Da, about 100 Da, about 150 Da, or about 200 Da. In some embodiments, any substituent can independently be optionally substituted alkyl (methyl, ethyl, or e.g. linear, branched, or cyclic $C_3$ alkyl, $C_4$ alkyl, $C_5$ alkyl, $C_6$ alkyl, $C_7$ alkyl, $C_8$ alkyl, etc.), —O-alkyl (e.g. —$OCH_3$, —$OC_2H_5$, —$OC_3H_7$, —$OC_4H_9$, etc.), COH, —CO-alkyl (e.g. —$COCH_3$, $COCH_2CH_3$, etc.), —S—alkyl (e.g. —$SCH_3$, —$SC_2H_5$, —$SC_3H_7$, —$SC_4H_9$, etc.), —NR'R", —OH, —SH, —CN, —$CF_3$, —$NO_2$, perfluoroalkyl, optionally substituted aryl, optionally substituted heteroaryl, optionally substituted amine, or a halogen, wherein R' and R" are independently H or optionally substituted alkyl. Wherever a substituent is described as "optionally substituted," that substituent can be substituted with the above substituents.

Some embodiments include an electron-transport compound that is useful, for example, in electron-transport elements of organic light emitting devices, which is represented by Formula 1:

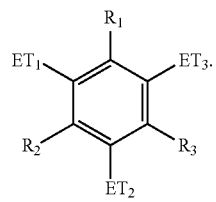

Formula 1

In some embodiments, $ET_1$ through $ET_3$ can be a substituent that can be an electron-transport material. In some embodiments, $ET_1$ through $ET_3$ can be a substituent that can comprise a quinolinyl group. In some embodiments, $ET_1$ through $ET_3$ can be a substituent that can comprise a quinoxalinyl group. In some embodiments, $ET_1$ through $ET_3$ can independently be substituted quinolinyl or optionally substituted quinoxalinyl. In some embodiments, $ET_1$, $ET_2$, and $ET_3$ are optionally substituted quinolinyl. In some embodiments, $ET_1$, $ET_2$, and $ET_3$ are optionally substituted quinoxalinyl. In some embodiments, $ET_1$, $ET_2$, and $ET_3$ are substituted onto the core molecule of Formula 1 through a bond on the benzo-ring of the optionally substituted quinolinyl or the optionally substituted quinoxalinyl. The term "benzo-ring" refers to the aryl ring structure of the quinolinyl or quinoxalinyl substituent. For example, the connecting bond on the benzo-ring can be through positions 5, 6, 7, or 8 in the following example reference systems:

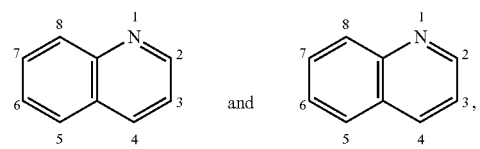

for quinolinyl and quinoxalinyl respectively. In some embodiments, $ET_1$, $ET_2$ or $ET_3$ can be bonded through the 5-yl position. In some embodiments, $ET_1$, $ET_2$ or $ET_3$ can be bonded through the 8-yl position. Those skilled in the art will recognize the nomenclature such that a 5-yl reference refers to a connecting bond at the 5 position, an 8-yl reference refers to a connecting bond at the 8 position, and so forth. In some embodiments $ET_1$ through $ET_3$ can be any of:

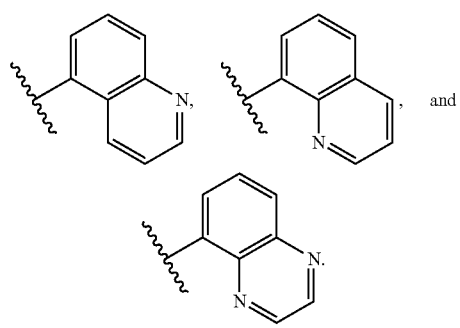

In some embodiments, $R_1$, $R_2$, and $R_3$, can independently be H, $C_{1-3}$ alkyl, or $C_{1-3}$ perfluoroalkyl.

Some embodiments include:

(ETC-1)

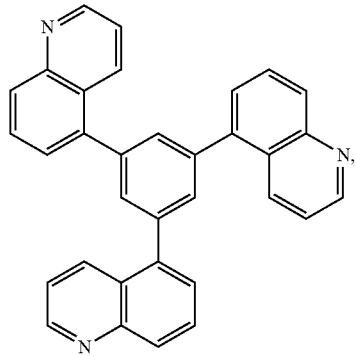

1,3,5-tri(quinolin-5-yl)benzene;

(ETC-2)

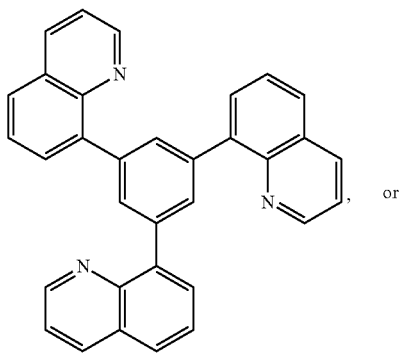

1,3,5-tri(quinolin-8-yl)benzene;

or (ETC-3)

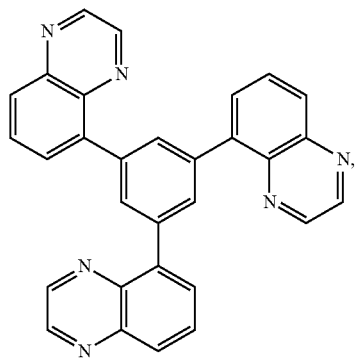

1,3,5-tri(quinoxalinyl-5-yl)benzene.

In some embodiments, an electron-transport element is provided comprising the aforementioned compounds, e.g., ETC-1, ETC-2, or ETC-3. In another embodiment, an electron-transport element is provided comprising any of the aforementioned light-emitting elements. In some embodiments, an organic light-emitting diode device is described comprising a cathode; an anode; a light-emitting layer; and an electron-transport layer disposed between and electrically connected to the cathode and the light-emitting layer wherein the electron-transport layer comprises an electron-transport compound described herein.

In some embodiments, a device is described further comprising a hole-transport layer between the anode and the light-emitting layer. In some embodiments, a device is described wherein the light-emitting layer further comprises an emissive component. In some embodiments, a device is described wherein the emissive component comprises a phosphorescent material. In some embodiments, a device is described wherein the organic light-emitting diode device comprises a cathode; an anode; a light-emitting layer disposed between and electrically connected to the anode and the cathode; a hole-transport layer between the anode and the light-emitting layer; and an electron-transport layer between the cathode and the light-emitting layer; wherein the electron-transport layer comprise an electron transporting compound described herein.

As shown in FIG. 1, an embodiment of an organic light emitting device incorporates the compounds of the present application. The embodiment also provides an organic light-emitting diode device 10 comprising a cathode 20, an anode 30, a light-emitting layer 40 disposed between and electrically connected to the anode 30 and the cathode 20, a hole-transport layer 50 between the anode 30 and the light-emitting layer 40 and an electron-transport layer 60 between the cathode 20 and the light-emitting layer 40, wherein the electron-transport layer can comprise an electron-transport compound described herein. In some embodiments, a hole-injection layer 70 can be between the anode 30 and the hole-transport layer 50. In some embodiments, an electron-injection layer (not shown) can be between the cathode 20 and the electron-transport layer 60.

An anode layer may include a material having a higher work function than the cathode, and may comprise a conventional material such as a metal, mixed metal, alloy, metal oxide or mixed-metal oxide, or a conductive polymer. Examples of suitable metals include the Group 1 metals, the metals in Groups 4, 5, 6, and the Group 8-10 transition metals. If the anode layer is to be light-transmitting, mixed-metal oxides of Group 12, 13, and 14 metals or alloys thereof, such as Au, Pt, and indium-tin-oxide (ITO), may be used. The anode layer may include an organic material such as polyaniline, e.g., as described in "Flexible light-emitting diodes made from soluble conducting polymer," Nature, vol. 357, pp. 477-479 (11 Jun. 1992). Examples of suitable high work function metals include but are not limited to Au, Pt, indium-tin-oxide (ITO), or alloys thereof. In some embodiments, the anode layer can have a thickness in the range of about 1 nm to about 1000 nm.

A cathode layer may include a material having a lower work function than the anode layer. Examples of suitable materials for the cathode layer include those selected from alkali metals of Group 1, Group 2 metals, Group 12 metals including rare earth elements, lanthanides and actinides, materials such as aluminum, indium, calcium, barium, samarium, and magnesium, and combinations thereof. Lithium-containing organometallic compounds, such as LiF, and $Li_2O$, may also be deposited between the organic layer and the cathode layer to lower the operating voltage. Suitable low work function metals include but are not limited to Al, Ag, Mg, Ca, Cu, Mg/Ag, LiF/Al, CsF, CsF/Al, or alloys thereof. In some embodiments, the cathode layer can have a thickness in the range of about 1 nm to about 1000 nm.

In some embodiments, the light-emitting layer may further comprise an emissive component or compound. The emissive component may be a fluorescent component and/or a phosphorescent compound. In some embodiments, the emissive component comprises a phosphorescent material. In some embodiments, the emissive component may comprise a dopant. In some embodiments, a dopant $Ir(piq)_2acac$ may be used. Suitable emissive materials are known to those skilled in the art. In some embodiments, the dopant is up to about 10% (w/w) of the host, or from about 0.1% (w/w) to about 5% (w/w) of the host.

The thickness of the light-emitting layer may vary. In some embodiments, the light-emitting layer has a thickness in the range of about 20 nm to about 200 nm. In some embodiments, the light-emitting layer has a thickness in the range of about 20 nm to about 150 nm.

In some embodiments, the light-emitting layer can further include additional host materials. Exemplary host materials are described in co-pending patent applications, e.g., United States Patent Application Publication No. US2012/0193614 (published Aug. 2, 2012, application Ser. No. 13/360,639, filed Jan. 27, 2012); United States Patent Application Publication No. US2012/0179089 (published Jul. 12, 2012, application Ser. No. 13/232,837, filed Sep. 14, 2011); United States Patent Application Publication No. US2011/0251401 (published Oct. 13, 2011, application Ser. No. 13/166,246, filed Jun. 22, 2011); U.S. Pat. No. 8,426,040, issued Apr. 23, 2013, and U.S. Pat. No. 8,263,238, issued Sep. 11, 2012, all of which are incorporated by reference in their entireties for their description of host materials. Other exemplary host materials to be included in the light-emitting layer include, but are not limited to, an optionally substituted compound selected from: an aromatic-substituted amine, an aromatic-substituted phosphine, a thiophene, an oxadiazole, 2-(4-biphenyl)-5-(4-tert-butylphenyl)-1,3,4-oxadiazole (PBD), 1,3-bis(N,N-t-butyl-phenyl)-1,3,4-oxadiazole (OXD-7), a triazole, 3-phenyl-4-(1'-naphthyl)-5-phenyl-1,2,4-triazole (TAZ), 3,4,5-triphenyl-1,2,3-triazole, 3,5-bis(4-tert-butyl-phenyl)-4-phenyl[1,2,4]triazole, an aromatic phenanthroline, 2,9-dimethyl-4,7-diphenyl-phenanthroline (bathocuproine or BCP), 2,9-dimethyl-4,7-diphenyl-1,10-phenanthroline, a benzoxazole, a benzothiazole, a quinoline, aluminum tris(8-hydroxyquinolate) (Alq3), a pyridine, a dicyanoimidazole, cyano-substituted aromatic, 1,3,5-tris(2-N-phenylbenzimidazolyl)benzene (TPBI), 4,4'-bis[N-(naphthyl)-N-phenyl-amino]biphenyl (α-NPD), N,N'-bis(3-methylphenyl)N,N'-diphenyl-[1,1'-biphenyl]-4,4'-diamine (TPD), 4,4'-bis[N,N'-(3-tolyl)amino]-3,3'-dimethylbiphenyl (M14), 4,4'-bis[N,N'-(3-tolyl)amino]-3,3'-dimethylbiphenyl (HMTPD), 1,1-bis(4-bis(4-methylphenyl)aminophenyl)cyclohexane, a carbazole, 4,4'-N,N'-dicarbazole-biphenyl (CBP), poly(9-vinylcarbazole) (PVK), N,N'N''-1,3,5-tricarbazoloylbenzene (tCP), a polythiophene, a benzidine, N,N'-bis(4-butylphenyl)-N,N'-bis(phenyl)benzidine, a triphenylamine, 4,4',4''-tris(N-(naphthylen-2-yl)-N-phenylamino)triphenylamine, 4,4',4''-tris(3-methylphenylphenylamino)triphenylamine (MTDATA), dibenzo[b,d]thiophene-2,8-diylbis(diphenylphosphine oxide) (PPT), 3,3'-di(9H-carbazol-9-yl)-1,1'-biphenyl (mCBP), a phenylenediamine, a polyacetylene, and a phthalocyanine metal complex.

In some embodiments, the light-emitting device may further comprise a hole-transport layer between the anode and the light-emitting layer and an electron-transport layer between the cathode and the light-emitting layer. In some embodiments, all of the light-emitting layer, the hole-transport layer and the electron-transport layer comprise a host compound described herein.

In some embodiments, a hole-transport layer may comprise at least one hole-transfer material. Exemplary hole-transport materials include: 1,1-bis(4-bis(4-methylphenyl)aminophenyl)cyclohexane; 2,9-dimethyl-4,7-diphenyl-1,10-phenanthroline; 3,5-Bis(4-tert-butyl-phenyl)-4-phenyl[1,2,4]triazole; 3,4,5-triphenyl-1,2,3-triazole; 4,4',4''-tris(N-(naphthylen-2-yl)-N-phenylamino)triphenylamine; 4,4',4''-tris(3-methylphenylphenylamino)triphenylamine (MTDATA); 4,4'-bis[N-(naphthyl)-N-phenyl-amino]biphenyl (α-NPD); 4,4'-bis[N,N'-(3-tolyl)amino]-3,3'-dimethylbiphenyl (HMTPD); 4,4'-bis[N,N'-(3-tolyl)amino]-3,3'-dimethylbiphenyl (M14); 4,4'-N,N'-dicarbazole-biphenyl (CBP); 1,3-N,N-dicarbazole-benzene (mCP); poly(9-vinylcarbazole) (PVK); a benzidine; a carbazole; a phenylenediamine; a phthalocyanine metal complex; a polyacetylene; a polythiophene; a triphenylamine; an oxadiazole; copper phthalocyanine; N,N'-bis(3-methylphenyl)N,N'-diphenyl-[1,1'-biphenyl]-4,4'-diamine (TPD); N,N'N''-1,3,5-tricarbazoloylbenzene (tCP); N,N'-bis(4-butylphenyl)-N,N'-bis(phenyl)benzidine; 4,4'-bis[N-(1-napthyl)-N-phenylamino] biphenyl (NPB), 4,4'4''-tri(N-carbazolyl)triphenylamine (TcTa) and the like.

In some embodiments, the electron-transport layer may comprise at least one of the electron-transfer materials comprising the compounds described above, e.g., ETC-1, ETC-2, or ETC-3.

If desired, additional layers may be included in the light-emitting devices disclosed herein. Additional layers that may be included include an electron-injection layer (EIL), a hole-blocking layer (HBL), an exciton-blocking layer (EBL), and/or a hole-injection layer (HIL). In addition to separate layers, some of these materials may be combined into a single layer. In addition to separate layers, some of these materials may be combined into other layers, e.g., an electron-blocking layer and/or an exciton-blocking layer can be combined into a hole-transport layer; or a hole-blocking layer and/or an exciton-blocking layer can be combined into an electron-transport layer.

In some embodiments, the device can include a hole-blocking layer, e.g., between the cathode and the light-emitting layer. Suitable hole-blocking materials that can be included in the hole-blocking layer include, but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton-blocking layer, e.g., between the light-emitting layer and the anode. In one embodiment, the band gap of the material(s) that comprise an exciton-blocking layer is large enough to substantially prevent the diffusion of excitons. A number of suitable exciton-blocking materials that can be included in the exciton-blocking layer include, but are not limited to, an optionally substituted compound selected from the following: aluminum quinolate (Alq3), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

In some embodiments, the light-emitting device includes a hole-injection layer, e.g., between the light-emitting layer and the anode. Suitable hole-injection materials that can be included in the hole-injection layer include, but are not limited to, an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenylbenzidine, poly(N,N'-bis(4-butylphenyl)-N,N'-bis(phenyl)benzidine), a triphenylamine or phenylenediamine derivative such as N,N'-bis(4-methylphenyl)-N,N'-bis(phenyl)-1,4-phenylenediamine, 4,4',4''-tris(N-(naphthylen-2-yl)-N-phenylamino)triphenylamine, an oxadiazole derivative such as 1,3-bis(5-(4-diphenylamino)phenyl-1,3,4- oxadiazol-2-yl)benzene, a polyacetylene derivative such as poly(1,2-bis-benzylthio-acetylene), and a phthalocyanine metal complex derivative such as phthalocyanine copper. Hole-injection materials, while still being able to transport holes, may have a hole mobility substantially less than the hole mobility of conventional hole-transport materials.

Those skilled in the art would recognize that the various materials described above can be incorporated in several different layers depending on the configuration of the device. In one embodiment, the materials used in each layer are selected to result in the recombination of the holes and electrons in the light-emitting layer.

Light-emitting devices comprising the compounds disclosed herein can be fabricated using techniques known in the art, as informed by the guidance provided herein. For example, a glass substrate can be coated with a high work functioning metal such as ITO which can act as an anode. After patterning the anode layer, a light-emitting layer that includes at least one compound disclosed herein can be deposited on the anode. The cathode layer, comprising a low work functioning metal (e.g., Mg:Ag), can then be vapor evaporated onto the light-emitting layer. If desired, the device can also include an electron-transport/injection layer, a hole-blocking layer, a hole-injection layer, an exciton-blocking layer and/or a second light-emitting layer that can be added to the device using techniques known in the art, as informed by the guidance provided herein.

Embodiments

The following embodiments are contemplated.

Embodiment 1. A compound represented by Formula 1:

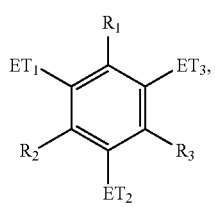

Formula 1 wherein $ET_1$, $ET_2$, and $ET_3$ are independently optionally substituted quinolinyl or optionally substituted quinoxalinyl, wherein the quinolinyl or quinoxalinyl attaches at a carbon atom of the benzo-ring; and $R_1$, $R_2$, and $R_3$ are independently H, $C_{1-3}$ alkyl, or $C_{1-3}$ perfluoroalkyl.

Embodiment 2. The compound of embodiment 1, wherein each substituent of quinolinyl and quinoxalinyl, if present, is represented by a formula $C_{0-6}H_{0-20}O_{0-3}N_{0-2}F_{0-5}Cl_{0-1}Br_{0-1}$, provided that each substituent has at least one non-hydrogen atom.

Embodiment 3. The compound of embodiment 1 or 2, wherein $R_1$ is H.

Embodiment 4. The compound of embodiment 1, 2, or 3, wherein $R_2$ is H.

Embodiment 5. The compound of embodiment 1, 2, 3, or 4, wherein $R_3$ is H.

Embodiment 6. The compound of embodiment 1, 3, 4, or 5, wherein $ET_1$, $ET_2$, and $ET_3$ are:

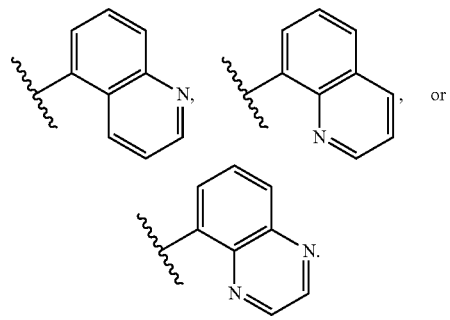

Embodiment 7. The compound of embodiment 1, wherein the compound is:

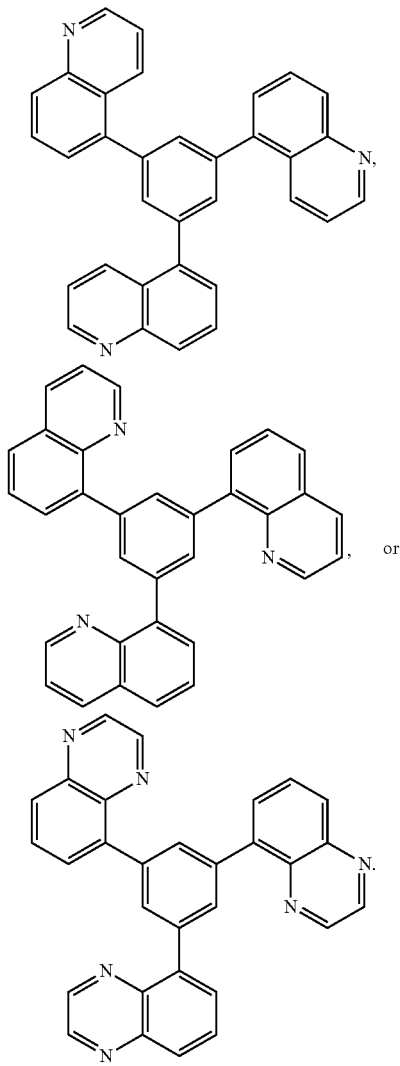

Embodiment 8. A compound that is optionally substituted 1,3,5-tri(quinoxalinyl-5-yl)benzene, optionally substituted 1,3,5-tri(quinolin-8-yl)benzene, or optionally substituted 1,3,5-tri(quinolin-5-yl)benzene.

Embodiment 9. An electron-transporting element comprising a compound of embodiment 1, 2, 3, 4, 5, 6, 7, or 8.

Embodiment 10. An organic light-emitting diode device comprising:
  (1) a cathode;
  (2) an anode;
  (3) a light-emitting layer disposed between and electrically connected to the anode and the cathode; and
  (4) the electron-transporting element of embodiment 9, in the form of an electron-transport layer disposed between and electrically connected to the cathode and the light-emitting layer.

Embodiment 11. The device of embodiment 10 further comprising a hole-transport layer between the anode and the light-emitting layer.

Embodiment 12. The device of embodiment 10 or 11, wherein the light-emitting layer further comprises an emissive component.

EXAMPLES

It has been discovered that embodiments of electron-transport elements described herein provide a new material that can be used in the interlayers of an OLED device. The benefits of these compounds are further shown by the following examples, which are intended to be illustrative of the embodiments of the disclosure, but are not intended to limit the scope or underlying principles in any way.

Example 1

Example 1 consists of synthesizing 1,3,5-tri(quinolin-5-yl)benzene (ETC-1), an embodied composition depicted above, by performing the reactions portrayed herein.

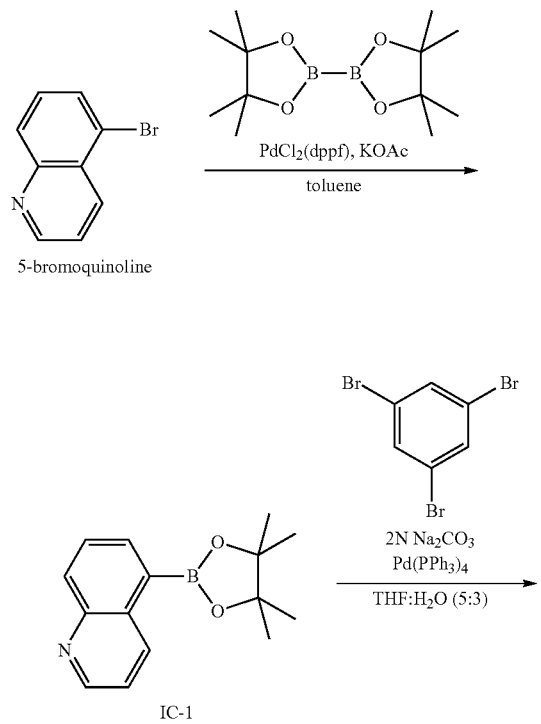

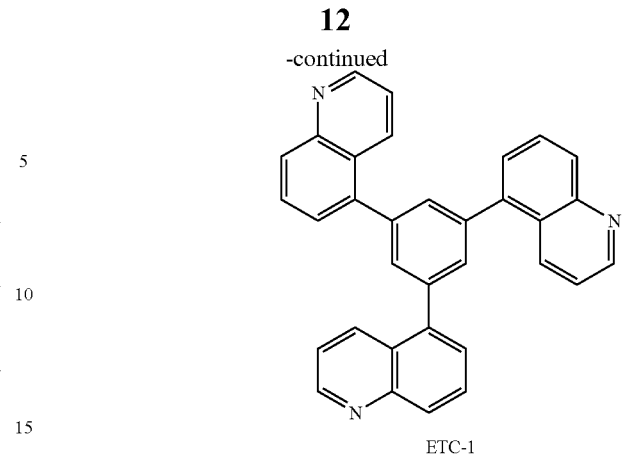

ETC-1

5-(4,4,5,5-tetramethyl-1,3,2-dioxaborolan-2-yl)quinoline (Intermediate Compound [IC] 1). A mixture of 5-bromoquinoline (2.50 g, 12.03 mmol) (TCI America, Portland, Oreg.), bis(pinacolato)diboron (6.42 g, 25.26 mmol) (Alfa Aesar, Ward Hill, Mass.), [1,1'-bis(diphenyl-phosphino)ferrocene]-dichloropalladium(II) (0.44 g, 0.60 mmol) (Frontier Scientific, Logan, Utah), potassium acetate (3.54 g, 36.09 mmol) (Aldrich, St. Louis, Mo.), and anhydrous toluene (70 mL) (Aldrich) was degassed with bubbling argon (Airgas, San Marcos, Calif.) for about 1 hour at room temperature. The reaction was then heated to about 100° C. in a hot plate with a silicone oil bath and was stirred overnight for 16 hours while maintaining an argon atmosphere. Consumption of the starting material was confirmed by thin-layer chromatography and the reaction was cooled to room temperature. The mixture was filtered and washed with dichloromethane (Alfa Aesar), and the filtrate was dried. The product was purified by silica gel column chromatography with acetone (Aldrich) in dichloromethane (Alfa Aesar) as the eluent. The product fractions were then dried and the product was collected to yield compound IC-1 (2.80 g, 91%). Confirmed by liquid-chromatograph-mass-spectrometer (LCMS) (using atmospheric pressure chemical ionization [APCI]) (Shimadzu Scientific Instruments, Tokyo, Japan): calculated for $C_{15}H_{18}BNO_2$ (M+H): 256; Found: 256.

1,3,5-tri(quinolin-5-yl)benzene (ETC-1). A mixture of IC-1 (2.58 g, 10.12 mmol), 1,3,5-tribromobenzene (1.03 g, 3.26 mmol) (Aldrich), tetrakis(triphenylphosphine) palladium(0) (0.23 g, 0.20 mmol), sodium carbonate (1.59 g, 15.00 mmol) (Alfa Aesar), tetrahydrofuran (25 mL) (Aldrich), and water (15 mL) was degassed with bubbling argon for 20 minutes at room temperature. The reaction was then heated to 85° C. on a hot plate with a silicone oil bath and was stirred overnight for 17 hours while maintaining an argon atmosphere. Consumption of the starting material was confirmed by thin-layer chromatography and the reaction was cooled to room temperature. The product was extracted with dichloromethane, dried, and purified by silica gel column chromatography with acetone in dichloromethane as the eluent. The product fractions were then dried and the product was collected to yield compound ETC-1 (1.18 g, 78%). Confirmed by LCMS (APCI): calculated for $C_{33}H_{21}N_3$ (M+H): 460; Found: 460.

Example 2

1,3,5-Tri(quinolin-8-yl)benzene (ETC-2), an embodied composition depicted above, was synthesized by performing the reactions portrayed herein.

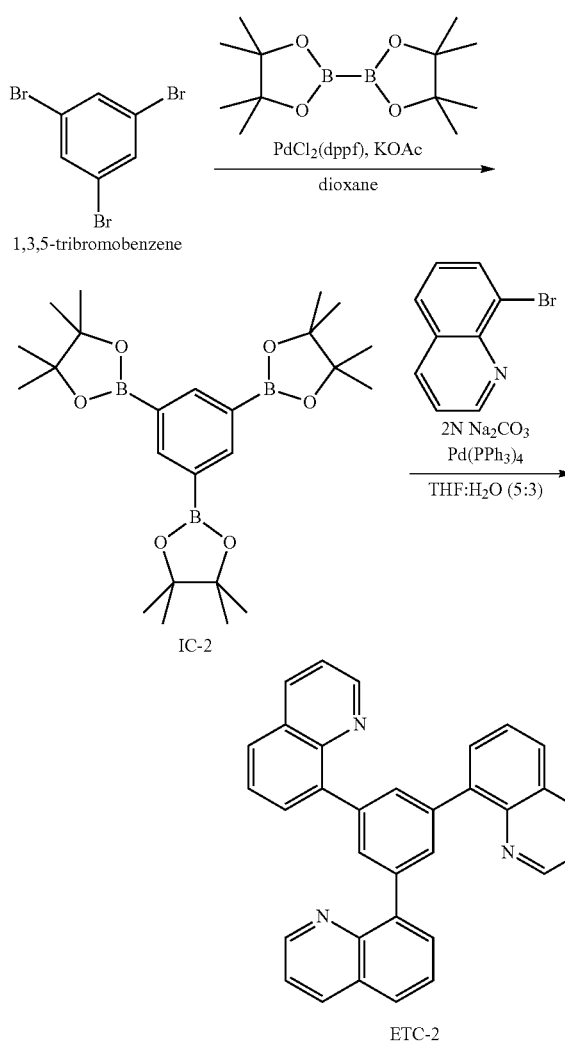

ETC-2

1,3,5-tris(4,4,5,5-tetramethyl-1,3,2-dioxaborolan-2-yl) benzene (IC-2). A mixture of 1,3,5-tribromobenzene (7.00 g, 22.24 mmol), bis(pinacolato)diboron (18.82 g, 74.11 mmol), [1,1'-bis(diphenyl-phosphino)ferrocene]-dichloropalladium (II) (1.79 g, 2.45 mmol), potassium acetate (14.84 g, 151.20 mmol), and anhydrous 1,4-dioxane (70 mL) (Aldrich) was degassed with bubbling argon for 30 minutes at room temperature. The reaction was then heated to 100° C. on a hot plate with a silicone oil bath and was stirred overnight for 16 hours while maintaining an argon atmosphere. Consumption of the starting material was confirmed by thin-layer chromatography and the reaction was cooled to room temperature. The mixture was filtered and washed with dichloromethane, and the filtrate was dried. The product was then recrystallized from hexanes (Aldrich). The recrystallized product was collected to yield compound IC-2 (7.66 g, 76%). Confirmed by LCMS (APCI): calculated for $C_{24}H_{39}B_3O_6$ (M+H): 457; Found: 457.

1,3,5-tri(quinolin-8-yl)benzene (ETC-2). A mixture of IC-2 (0.75 g, 1.6 5 mmol), 8-bromoquinoline (1.06 g, 5.10 mmol) (Aldrich), tetrakis(triphenylphosphine) palladium(0) (0.17 g, 0.15 mmol) (Frontier Scientific), sodium carbonate (1.59 g, 15.00 mmol) (Aldrich), tetrahydrofuran (25 mL) (Aldrich), and water (15 mL) was degassed with bubbling argon for 30 minutes at room temperature. The reaction was then heated to 85° C. on a hot plate with a silicone oil bath and was stirred for 1 day maintaining an argon atmosphere. Consumption of the starting material was confirmed by thin-layer chromatography and the reaction was cooled to room temperature. The product was extracted with dichloromethane, dried, and purified by silica gel column chromatography with acetone in dichloromethane as the eluent. The product fractions were then dried and the product was collected to yield ETC-2 (0.68 g, 90%). Confirmed by LCMS (APCI); calculated for $C_{33}H_{21}N_3$ (M+H): 460; Found: 460.

Example 3

1,3,5-Tri(quinoxalinyl-5-yl)benzene (ETC-3), an embodied composition depicted above, was synthesized by performing the reactions portrayed herein.

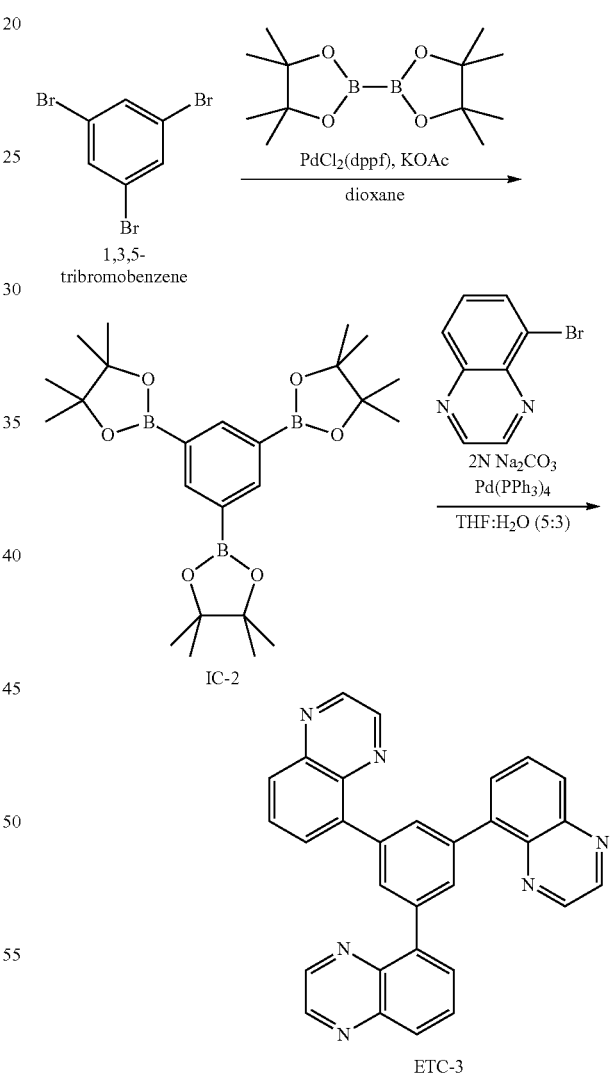

ETC-3

1,3,5-tris(4,4,5,5-tetramethyl-1,3,2-dioxaborolan-2-yl) benzene (Intermediated Compound 2 [IC-2]). A mixture of 1,3,5-tribromobenzene (7.00 g, 22.24 mmol), bis(pinacolato)diboron (18.82 g, 74.11 mmol), [1,1'-bis(diphenyl-phosphino)ferrocene]-dichloropalladium(II) (1.79 g, 2.45 mmol), potassium acetate (14.84 g, 151.20 mmol), and anhydrous 1,4-dioxane (70 mL) was degassed with bubbling argon for 30 minutes at room temperature. The reaction was then heated to 100° C. on a hot plate with a silicone oil bath and was stirred overnight for 16 hours while maintaining an argon atmosphere. Consumption of the starting material was confirmed by thin-layer chromatography and the reaction was cooled to room temperature. The mixture was filtered and washed with dichloromethane, and the filtrate was dried. The product was then recrystallized from hexanes. The recrystallized product was collected to yield compound IC-2 (7.66 g, 76%). Confirmed by LCMS (APCI): calculated for $C_{24}H_{39}B_3O_6$ (M+H): 457; Found: 457.

1,3,5-tri(quinoxalinyl-5-yl)benzene (ETC-3). A mixture of IC-2 (0.68 g, 1.50 mmol), 5-bromoquinoxalinyl (0.94 g, 4.49 mmol) (Aldrich), tetrakis(triphenylphosphine) palladium(0) (0.16 g, 0.13 mmol) (Frontier Scientific), sodium carbonate (1.59 g, 15.00 mmol), tetrahydrofuran (25 mL), and water (15 mL) was degassed with bubbling argon for 1 hour at room temperature. The reaction was then heated to 85° C. on a hot plate with a silicone oil bath and was stirred for 1 day maintaining an argon atmosphere. Consumption of the starting material was confirmed by thin-layer chromatography and the reaction was cooled to room temperature. The product was extracted with dichloromethane, dried, and purified by silica gel column chromatography with methanol in dichloromethane as the eluent. The product fractions were then dried and the product was recrystallized from acetone. The recrystallized product was collected to yield compound ETC-3 (0.43 g, 62%). Confirmed by LCMS (APCI): calculated for $C_{30}H_{18}N_6$ (M+H): 460; Found: 463.

Example 4

Fabrication of light-emitting device: the ITO-coated glass substrates are cleaned by ultrasound in detergent solution, DI water, acetone, and 2-propanol consecutively, then baked at 110° C. for about 3 hours, and followed by treatment with oxygen plasma for about 30 minutes. A layer of PEDOT:PSS (HIL 1.1 purchased from H.C. Starck) is then spin-coated at 4000 rpm onto the pre-cleaned and $O_2$-plasma treated (ITO)-substrate and annealed at 180° C. for about 30 minutes, yielding a thickness of around 40 nm. In a glove-box hosted vacuum deposition system at a pressure of $10^{-7}$ torr (1 torr=133.322 Pa), NPB is first deposited on top of PEDOT/PSS layer at deposition rate of 0.1 nm/s, yielding a 40 nm thick film. A 20 nm-thick layer of N-phenyl-N-(4'''-(1-phenyl-1H-benzo[d]imidazol-2-yl)-[1,1':4',1'':4'',1'''-quaterphenyl]-4-yl)naphthalen-1-amine (see U.S. Pat. No. 8,426,040) doped with red phosphorescent emitter Ir(piq)$_2$acac by 10 wt % is deposited by co-deposition on top of NPB. Subsequently a 30 nm thick layer of ETC-1 at a deposition rate of about 0.1 nm/s will be deposited. The device is completed by LiF (1 nm) and Al (100 nm) layers deposited successively at deposition rates of 0.015 and 0.3 nm/s, respectively. Each individual device has an area of 0.04 mm². The current-voltage-brightness (I-V-L) characteristics and EL spectra of the devices are measured by a programmable Keithley 2400 sourcemeter (Keithley Instruments, Inc., Cleveland, Ohio) and a PhotoResearch PR-670 spectroradiometer (Photo Research, Inc., Chatsworth, Calif.). All device operation is carried out inside a nitrogen-filled glove-box.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing embodiments of the present disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosed embodiments and does not pose a limitation on the scope of any claim. No language in the specification should be construed as indicating any non-claimed element essential to the practice of the embodiments of this disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the objects of this disclosure. Of course, variations on these described embodiments will become apparent to those of ordinary skill in the art upon reading the foregoing description. The inventor expects skilled artisans to employ such variations as appropriate, and the inventors intend for the embodiments disclosed herein to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:
1. A compound represented by Formula 1:

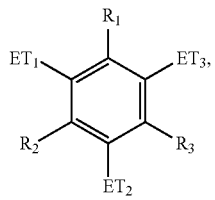

Formula 1

I. wherein ET$_1$, ET$_2$, and ET$_3$ are independently optionally substituted quinolinyl or optionally substituted quinoxalinyl, wherein the quinolinyl or quinoxalinyl attaches at a carbon atom of the benzo-ring;
II. R$_1$, R$_2$, and R$_3$ are independently H, C$_{1-3}$ alkyl, or C$_{1-3}$ perfluoroalkyl; and
III. wherein ET$_1$, ET$_2$, and ET$_3$ are:

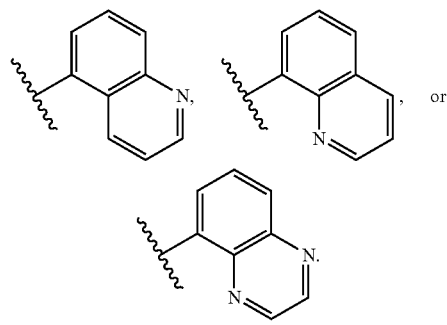

2. The compound of claim 1, wherein R$_1$ is H.
3. The compound of claim 1, wherein R$_2$ is H.
4. The compound of claim 1, wherein R$_3$ is H.
5. The compound of claim 1, wherein the compound is:

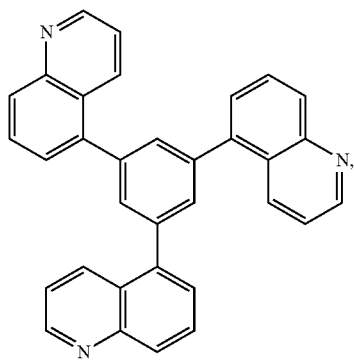

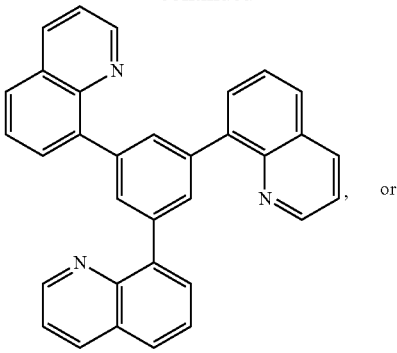

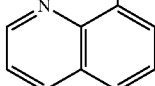

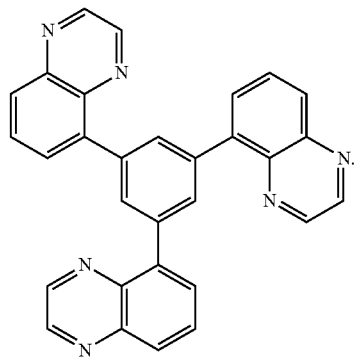

6. An electron-transporting element comprising a compound of claim 1.

7. An organic light-emitting diode device comprising:
(1) a cathode;
(2) an anode;
(3) a light-emitting layer disposed between and electrically connected to the anode and the cathode; and
(4) the electron-transporting element of claim 6, in the form of an electron-transport layer disposed between and electrically connected to the cathode and the light-emitting layer.

8. The device of claim 7, further comprising a hole-transport layer between the anode and the light-emitting layer.

9. The device of claim 7, wherein the light-emitting layer further comprises an emissive component.

* * * * *